(12) United States Patent
Yokoyama et al.

(10) Patent No.: US 8,759,100 B2
(45) Date of Patent: *Jun. 24, 2014

(54) METHOD OF CELL CULTURE (75) Inventors: Naoki Yokoyama, Tokyo (JP); Tomonori Akai, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/990,642

(22) PCT Filed: Dec. 6, 2010

(86) PCT No.: PCT/JP2010/071831
§ 371 (c)(1),
(2), (4) Date: May 30, 2013

(87) PCT Pub. No.: WO2012/077175
PCT Pub. Date: Jun. 14, 2012

(65) Prior Publication Data
US 2013/0244328 A1    Sep. 19, 2013

(51) Int. Cl.
*C12N 5/00*      (2006.01)
(52) U.S. Cl.
USPC .......................................................... 435/401
(58) Field of Classification Search
None
See application file for complete search history.

(56) References Cited

U.S. PATENT DOCUMENTS

| 7,687,251 B2 | 3/2010 | Hattori et al. |
| 2005/0279730 A1 | 12/2005 | Miyake et al. |
| 2007/0274968 A1 | 11/2007 | Hattori et al. |
| 2010/0184182 A1 | 7/2010 | Hase |
| 2010/0184222 A1 | 7/2010 | Hase |
| 2010/0190246 A1 | 7/2010 | Hase |

FOREIGN PATENT DOCUMENTS

| JP | 2245181 A | 9/1990 |
| JP | 2005-261432 A | 9/2005 |
| JP | 2005-270055 A | 10/2005 |
| JP | 2007-312736 A | 12/2007 |
| JP | 2009-50201 A | 3/2009 |
| JP | 2010-119304 A | 6/2010 |
| JP | 2010-200620 A | 6/2010 |
| JP | 2010-161952 A | 7/2010 |
| JP | 2010-161953 A | 7/2010 |
| JP | 2010-161954 A | 7/2010 |

OTHER PUBLICATIONS

Shah, S. S., et al., "Exercising Spatiotemporal Control of Cell Attachment with Optically Transparent Microelectrodes", Langmuir, May 30, 2008, vol. 24(13), pp. 6837-6844.

Jiang, et al., "Electrochemical desorption of self-assembled monolayers noninvasively releases patterned cells from geometrical confinements", J. Am. Chem. Soc., 125: 2366-7.

*Primary Examiner* — Suzanne M Noakes
*Assistant Examiner* — Stephen Chong
(74) *Attorney, Agent, or Firm* — Lucas & Mercanti, LLP (57) ABSTRACT

This invention provides a means for modifying surface properties of a cell culture substrate under specific conditions, to thereby regulate regions to which cells are allowed to adhere or are not allowed to adhere, depending on cell type. This invention relates to a method of cell culture comprising steps of: applying a positive potential to a conductive region of a substrate comprising a base material having a conductive region and a non-cell-adhesive membrane coupled thereto with the aid of silane, so as to separate the non-cell-adhesive membrane from the substrate; and culturing cells in a region from which the non-cell-adhesive membrane has been separated.

12 Claims, 4 Drawing Sheets

Fig. 4

METHOD OF CELL CULTURE

CROSS-REFERENCE TO RELATED APPLICATIONS

This application is a 371 of PCT/JP2010/071831, filed Dec. 6, 2010, the contents of which are incorporated herein by reference.

TECHNICAL FIELD

The present invention relates to a method for culturing cells on a substrate with modifiable surface properties.

BACKGROUND ART

At present, a wide variety of animal and plant cells are cultured, and novel cell culture techniques are being developed. Cell culture techniques are conducted for the purpose of elucidation of biochemical phenomena and cell properties, production of useful substances, and other purposes. In addition, inspection of physiological activity or toxicity of artificially synthesized drugs has been attempted with the use of cultured cells.

Some cells (many animal cells, in particular) have adhesion-dependent properties, such that they grow while adhering to other substances. Thus, such cells cannot survive for a long period of time if they are in suspension outside an organism. Culture of such adhesion dependent cells necessitates the use of a support to which cells adhere, and a plastic culture dish that is evenly coated with a cell-adhesive protein, such as collagen or fibronectin, is generally used. Such cell-adhesive protein is known to act on cultured cells, facilitate cell adhesion, and influence cellular configurations.

In order to evaluate functions of cells that survive while adhering to other substances in vivo, accordingly, it is necessary that cells be cultured while adhering to other substances. When cell-to-cell interactions are to be evaluated, it is also preferable that adhered cells be subjected to co-culture and interactions be evaluated. Even though it has been possible for cells to adhere to specific regions that have been selectively made cell-adhesive on a support, it has been difficult to cause two or more types of cells separately adhere to different regions. Accordingly, development of techniques that enable modification of cell adhesiveness under given conditions and regulation of regions to which cells are allowed to adhere or are not allowed to adhere, depending on cell type, has been awaited.

Non-Patent Document 1 describes that cells that had adhered to specific regions on a substrate that is not patterned and is conductive across its entire surface are released and diffused from such regions upon application of potentials. However, Non-Patent Document 1 does not describe that a conductive region is converted into a cell-adhesive region upon application of potentials. In addition, Non-Patent Document 1 does not describe regulation of regions to which cells are allowed to adhere.

Non-Patent Document 2 describes a method of cell culture comprising forming a non-cell-adhesive membrane on a base material upon which a conductive region and an insulating region are provided, applying an electric potential to a given conductive region to modify the non-cell-adhesive membrane into a cell-adhesive membrane, and allowing cells to adhere selectively to such region.

BACKGROUND OF THE INVENTION

Non-Patent Documents

Non-Patent Document 1: Jiang, X., Ferrigno, R. Mrksich, M., and Whitesides, a M., 2003, Electrochemical desorption of self-assembled monolayers noninvasively releases patterned cells from geometrical confinements, J. Am. Chem. Soc., 125: 23667

Non-Patent Document 2: Sunny, S., Shah, Ji Youn Lee, Stanislav Verkhoturov, Nazgul Tuleuova, Emile A. Schweikert, Erlan Ramanculov, and Alexander Revzin, 2008, Exercising Spatiotemporal Control of Cell Attachment with Optically Transparent Microelectrodes, Langmuir 24: 6837-6844

SUMMARY OF THE INVENTION

Object to be Attained by the Invention

The present inventors had attempted to convert a non-cell-adhesive membrane into a cell-adhesive membrane by providing a non-cell-adhesive membrane on a base material with conductive regions and applying negative potentials to the conductive regions in accordance with the method described in Non-Patent Document 2. However, they discovered that a non-cell-adhesive membrane cannot be converted into a cell-adhesive membrane via application of a negative potential, cells cannot adhere to the membrane even if cells are seeded, and observation of cultured cells becomes difficult due to the blackening of the conductive regions resulting from the application of negative potentials.

The present invention is intended to provide a means for modifying surface properties of a cell culture substrate under specific conditions, to thereby regulate regions to which cells are allowed to adhere or are not allowed to adhere, depending on cell type.

Means for Attaining the Object

The present inventors discovered that, upon application of a positive potential to a conductive region of a substrate comprising a non-cell-adhesive membrane coupled to the conductive region with the aid of silane, a non-cell-adhesive membrane could be degraded and converted into a cell-adhesive region. This has led to the completion of the present invention.

Specifically, the present invention includes the following.

(1) A method of cell culture comprising steps of; applying a positive potential to a conductive region of a substrate comprising a base material having a conductive region and a non-cell-adhesive membrane coupled thereto with the aid of silane, so as to separate the non-cell-adhesive membrane from the substrate; and culturing cells in a region from which the non-cell-adhesive membrane has been separated.

(2) The method according to (1), wherein the conductive region comprises an indium tin oxide membrane on the base material surface.

(3) The method according to (1) or (2), wherein the non-cell-adhesive membrane is a non-cell-adhesive hydrophilic membrane composed of an organic compound.

(4) The method according to (3), wherein the organic compound is an alkylene glycol oligomer.

(5) The method according to any of (1) to (4), wherein a positive potential of 1 to 10 V is applied to the conductive region.

(6) The method according to any of (1) to (5), wherein the positive potential is applied for 0.5 to 60 minutes.

(7) A method of cell culture comprising steps of: fixing a protein on a membrane of a substrate comprising a base material having a conductive region and a non-cell-adhesive membrane coupled thereto with the aid of silane, so as to form a protein layer; culturing cells on the protein layer; and applying a positive potential to the conductive region, so as to separate cells together with the protein layer from the substrate.

(8) The method according to (7), wherein the conductive region comprises an indium tin oxide membrane on the base material surface.

(9) The method according to (7) or (8), wherein the non-cell-adhesive membrane is a non-cell-adhesive hydrophilic membrane composed of an organic compound.

(10) The method according to (9), wherein the organic compound is an alkylene glycol oligomer.

(11) The method according to any of (7) to (10), wherein a positive potential of 1 to 10 V is applied to the conductive region.

(12) The method according to any of (7) to (11), wherein the positive potential is applied for 0.5 to 60 minutes.

Effects of the Invention

According to the present invention, surface properties of a cell culture substrate can be modified under specific conditions, to thereby regulate regions to which cells are allowed to adhere or are not allowed to adhere, depending on cell type, co-culture of different types of cells and evaluation of interactions can be performed, and cells that have been cultured while adhering to other substances can be collected.

EMBODIMENTS FOR CARRYING OUT THE INVENTION

The method of cell culture according to an embodiment of the present invention involves the use of a substrate comprising a base material having a conductive region and a non-cell-adhesive membrane coupled thereto with the aid of silane. The method comprises steps of: applying a positive potential to a conductive region on the substrate, so as to separate the non-cell-adhesive membrane from a substrate; and culturing cells in a region from which the non-cell-adhesive membrane has been separated.

(Base Material)

The base material that is used in the present invention is not particularly limited, provided that it comprises a material capable of forming a conductive region. A base material with conductive regions and insulating regions is preferable. By forming a patterned configuration of conductive regions as a plurality of independent regions isolated by insulating regions, positive potentials can be selectively applied to specific regions, and such specific regions can be selectively converted into cell-adhesive regions. A base material with conductive regions and insulating regions can be prepared by, for example, forming conductive regions on a base material comprising an insulating material. In addition, a preferable base material has a surface coated with an organic compound. Further, a conductive region is preferably a cell-adhesive region.

Specific examples include glass, silica glass, borosilicate glass, alumina, sapphire, ceramics, forsterite, photosensitive glass, ceramic, silicon, elastomer, and organic materials represented by plastics (e.g., polyester resin, polyethylene resin, polypropylene resin, ABS resin, nylon, acrylic resin, fluorocarbon resin, polycarbonate resin, polyurethane resin, methylpentene resin, phenolic resin, melamine resin, epoxy resin, and vinyl chloride resin). The configuration thereof is not limited, and examples include: two-dimensional configurations, such as flat plates, flat membranes, films, and porous membranes; three-dimensional configurations, such as cylinders, stamps, multi-well plates, and microchannels; and configurations having concave-convex patterns on their surfaces. When a film is used, the thickness thereof is not particularly limited, and it is generally 0.1 μm to 1,000 μm, preferably 1 μm to 500 μM, and more preferably 10 μm to 200 μm.

When a base material having a fine concave-convex pattern of about 1 nm to 10 μm that is smaller than the size of a cell provided on its surface is used and a cell-adhesive region in a conductive region and an insulating region have similar configurations, in particular, the configurations and behavior of the adhered cells, may be regulated so as to effectively conduct assays. The term "fine concave-convex" refers to, for example, a depth of 1 nm to 10 μm, a convex line width of 1 nm to 10 μm, and a concave line width of 1 nm to 10 μm, in the case of line patterns.

When a conductive region is provided on a base material comprising an insulating material, a conventional patterning technique can be employed. Examples of conventional patterning techniques include various printing techniques, such as gravure printing, screen printing, offset printing, flexography, and contact printing, various lithography techniques, inkjet methods, and three-dimensional shaping, such as carving of fine grooves. Specifically, a conductive material, such as a metal or metal oxide membrane, is provided on a base material comprising an insulating material, such as a glass base material, and the resulting membrane is subjected to a conventional patterning technique, such as photolithography. Thus, a conductive region and an insulating region can be provided.

A conductive membrane can be provided on a base material in accordance with a conventional technique. Examples thereof include microwave plasma chemical vapor deposition (CVD), electric cyclotron resonance chemical vapor deposition (ECRCVD), inductive coupled plasma (ICP), DC sputtering, electric cyclotron resonance (ECR), sputtering, ionized vapor deposition, arc vapor deposition, laser vapor deposition, electron beam (EB) vapor deposition, and resistance heating vapor deposition techniques. A membrane may be provided by coating. Spin coating and various printing techniques can also be employed.

Examples of conductive membranes constituting a conductive region include a metal membrane or a metal oxide membrane, a membrane comprising metal fine particles or metal nanofibers dispersed throughout an insulator, and a membrane comprising a conductive organic material. Examples of metal oxides include indium tin oxide (ITO) and indium zinc oxide (IZO). Examples of metal fine particles include silver, gold, and copper fine particles. An example of metal nanofibers is carbon nanotubes. An example of a conductive organic material is polyethylenedioxythiophene (PEDOT).

A conductive membrane is not particularly limited, and a transparent membrane is preferable. Examples thereof include an ITO membrane, an IZO membrane, and a conductive polymeric membrane, such as a polyethylenedioxythiophene membrane. In the present invention, it is preferable that a conductive region be provided by forming an ITO membrane by sputtering, followed by patterning.

The thickness of a conductive membrane is generally from that of a monomolecular membrane to approximately 100 µm, preferably 2 nm to 1 µm, and more preferably 5 nm to 500 nm.

Specifically, patterning of the conductive region as described above can be performed by subjecting the prepared metal membrane or metal oxide membrane to resist coating, exposure using a photomask, development, and etching.

The pattern configuration of the conductive region can be any two-dimensional configuration without particular limitation, and it can be selected in accordance with, for example, cell type and tissue to be formed. For example, the pattern configuration can be line-shaped, tree-shaped (dendroid), netlike, lattice-shaped, circular, or square, and a circular or square figure in which the entire area constitutes a conductive region or an insulating region can be formed.

(Non-Cell-Adhesive Membrane)

A non-cell-adhesive membrane is bound to a conductive region of a base material with the aid of silane, and it is preferably a non-cell-adhesive hydrophilic membrane composed of an organic compound. Such hydrophilic membrane is not particularly limited, provided that it is a thin membrane made mainly from a water-soluble or water-swelling organic compound, and preferably an organic compound containing a carbon-oxygen bond, which is non-cell-adhesive before a positive potential is applied to the conductive region and degrades and separates from the substrate after a positive potential has been applied.

In the present invention, the term "carbon-oxygen bond" refers to a bond between carbon and oxygen, and it may be a single or a double bond. Examples of carbon-oxygen bonds include C—O, C(=O)—O, and C=O.

Examples of organic compounds serving as main components include a water-soluble polymer, a water-soluble oligomer, a water-soluble organic compound, a surfactant, and an amphiphilic agent. These substances physically or chemically crosslink to each other, the resultant binds to a conductive region of the base material with the aid of silane, and a hydrophilic thin membrane can then be obtained.

Specific examples of water-soluble polymeric materials include polyalkylene glycol and a derivative thereof, polyacrylic acid and a derivative thereof, polymethacrylic acid and a derivative thereof, polyacrylamide and a derivative thereof, polyvinyl alcohol and a derivative thereof, a zwitterionic polymer, and a polysaccharide. A molecular configuration can be, for example, line-shaped, branched, or dendrimeric. More specific examples include, but are not limited to, polyethylene glycol, a copolymer of polyethylene glycol and polypropylene glycol, such as Pluronic F108 and Pluronic F127, poly(N-isopropylacrylamide), poly(N-vinyl-2-pyrrolidone), poly(2-hydroxyethyl methacrylate), poly (methacryloyloxyethyl phosphorylcholine), a copolymer of methacryloyloxyethyl phosphorylcholine and acrylic monomer, dextran, and heparin.

Specific examples of water-soluble oligomeric materials and water-soluble low-molecular-weight compounds include an alkylene glycol oligomer and a derivative thereof, an acrylate oligomer and a derivative thereof, a methacrylate oligomer and a derivative thereof, an acrylamide oligomer and a derivative thereof, a saponification product of a vinyl acetate oligomer and a derivative thereof, an oligomer comprising zwitterionic monomers and a derivative thereof, an acrylic acid and a derivative thereof, a methacrylic acid and a derivative thereof, an acrylamide and a derivative thereof, a zwitterionic compound, a water-soluble silane coupling agent, and a water-soluble thiol compound. More specific examples include, but are not limited to, an ethylene glycol oligomer, an (N-isopropylacrylamide) oligomer, a methacryloyloxyethyl phosphorylcholine oligomer, low-molecular-weight dextran, low-molecular-weight heparin, oligoethylene glycol thiol, ethylene glycol, diethylene glycol, triethylene glycol, tetraethylene glycol, 2-[methoxy(polyethyleneoxy)-propyltrimethoxysilane], and Methylene glycol-terminated-thiol.

It is preferable that a non-cell-adhesive membrane have high non-cell-adhesiveness before application of a positive potential and be separated from the base material after application of a positive potential.

The average thickness of a non-cell-adhesive membrane is preferably 0.8 nm to 500 µm, more preferably 0.8 nm to 100 µm, further preferably 1 nm to 10 µm, and most preferably 1.5 nm to 1 µm. An average thickness of at least 0.8 nm is preferable since protein adsorption and cell adhesion are less likely to be influenced by a region that is not covered by a membrane on the substrate surface. If the average thickness is 500 µm or less, coating can be performed in a relatively simple manner.

A non-cell-adhesive membrane is bound to a base material surface with the aid of silane serving as a binding layer. Preferably, a silane layer serving as a binding layer is provided on a base material, and the resultant is then coated with an organic compound. A non-cell-adhesive membrane bound to a conductive region of a base material with the aid of silane can be degraded and removed via application of a positive potential to a conductive region, and surface properties of a base material can be modified. A silane-mediated bond can be formed by coating a base material having a conductive region with a silane coupling agent having a functional group that can form a covalent bond with a functional group of an organic compound and further coating the base material with an organic compound. Examples of combinations of functional groups that can form covalent bonds include an epoxy group and a hydroxyl group, phthalic anhydride and a hydroxyl group, a carboxyl group and N-hydroxysuccinimide, a carboxyl group and carbodiimide, and an amino group and glutaraldehyde. Preferably, a base material is coated with a silane coupling agent having an epoxy group at its terminus (i.e., epoxysilane) to form a silane layer, followed by coating with an alkylene glycol-based material (including polyalkylene glycol, alkylene glycol oligomer, and a derivative thereof), and more preferably with an ethylene glycol-based material (preferably triethylene glycol), in the presence of an acid catalyst.

In the case of a silane coupling agent having an epoxy group at its terminus, for example, the water contact angle on the surface of the silane layer before a non-cell-adhesive membrane containing an organic compound is formed is typically 10 degrees to 43 degrees, and preferably 15 degrees to 40 degrees.

(Separation of Non-Cell-Adhesive Membrane)

In the present invention, a positive potential is applied to a conductive region of a substrate comprising a non-cell-adhesive membrane coupled to a conductive region with the aid of silane, so as to separate the non-cell-adhesive membrane from the substrate and convert the region into a cell-adhesive region.

According to the present invention, the term "cell adhesiveness" (and variations thereof) refers to a condition in which a cell adheres to a substance of interest or a cell is likely to adhere to a substance of interest. In contrast, the term "non-cell-adhesiveness" (and variations thereof) refers to a condition in which a cell is less likely to adhere to a substance or a cell does not adhere to a substance. When cells are seeded on a substrate comprising cell-adhesive regions and non-cell-adhesive regions in a patterned manner, accordingly, cells adhere to cell-adhesive regions, but cells do not adhere to non-cell-adhesive regions. Thus, cells would be aligned in a patterned manner on the substrate surface.

Since cell adhesiveness can vary depending on types of cells to adhere, the term "cell adhesiveness" refers to a condition in which a substance has adhesiveness to a given type of cell. Accordingly, a plurality of cell-adhesive regions corresponding to a plurality of types of cells may be present on a cell culture substrate; that is, two or more different cell-adhesive regions with different degrees of cell adhesiveness may be present. The same applies to the condition represented by the term "non-cell adhesiveness,"

The present inventors discovered that, upon application of a positive potential to a conductive region, a non-cell-adhesive membrane bound with the aid of silane can be degraded and modified into a cell-adhesive region. The term "degradation (and variations thereof)" used herein refers to a change in which a bond of an organic compound is cleaved and two or more types of organic compounds are generated from a single type of organic compound. According to the present invention, a bond between an organic compound and silane is cleaved upon application of a positive potential to a conductive region, and at least part of an organic compound constituting a non-cell-adhesive membrane is then degraded or removed.

As the concentration of an organic compound bound to a base material with the aid of silane increases, cell adhesion becomes less likely to occur. Accordingly, separation of a non-cell-adhesive membrane also involves modification of a membrane comprising an organic compound at high concentration into a membrane comprising an organic compound at low concentration that allows cell adhesion.

A non-cell-adhesive membrane and a cell-adhesive membrane can be evaluated by contact angle measurements, ellipsometry, atomic force microscope observation, electron microscope observation, Auger electron spectroscopy, X-ray photoelectron spectroscopy, various mass spectrometry techniques, and other techniques. As the concentration of an organic compound increases in the membrane (preferably, as carbon content increases), cell adhesion becomes less likely to occur. Accordingly, cell adhesiveness and non-cell adhesiveness can be evaluated by measuring carbon content. X-ray photoelectron spectroscopy (XPS/ESCA) is thus preferable. The relative quantitative value is determined by such technique in terms of atomic concentration (%), in general. Specifically, measurement can be carried out in accordance with the method described in JP Patent Publication (Kokai) No. 2007-312736 A.

A positive potential to be applied to a conductive region is generally 1 to 10 V, and preferably 2 to 5 V. The duration during which a positive potential is applied is generally 0.5 to 60 minutes, and preferably 1 to 10 minutes.

The present inventors discovered that cell observation would become difficult because of blackening resulting from application of a negative potential to a conductive region composed of a transparent ITO membrane. They also discovered that an ITO membrane would remain transparent if a positive potential is applied under the conditions described above and cell observation could be satisfactorily performed. In addition, they discovered that, while a membrane cannot be separated when a negative potential is applied to a conductive region to which a non-cell-adhesive membrane has been bound, a membrane could be separated by application of a positive potential.

(Cells)

According to the present invention, cells to be cultured can be floating cells, such as blood cells and lymphoid cells, or adhesive cells, and the present invention is preferably used for cells having adhesiveness. The present invention is also preferable for cells capable of migration. Examples of such cells include: cancer cells, such as hepatic cancer cells, glioma cells, colon cancer cells, renal cancer cells, pancreatic cancer cells, prostate cancer cells, bowel cancer cells, breast cancer cells, lung cancer cells, and ovarian cancer cells; hepatic cells that are the parenchymal cells of the liver; endothelial cells, such as Kupffer cells, vascular endothelial cells, and corneal endothelial cells; epidermal cells, such as fibroblasts, osteoblasts, osteoclasts, cells of the periodontal ligament, and epidermal keratinocytes; epidermal cells, such as tracheal epithelial cells, gastrointestinal epithelial cells, cervical epithelial cells, and corneal epithelial cells; mammary gland cells; pericytes; muscle cells, such as smooth muscle cells and cardiac muscle cells; renal cells; pancreatic islet cells; nerve cells, such as peripheral nerve cells and optic nerve cells; cartilage cells; and osteocytes. These cells may be primary cells directly sampled from tissue or organs or cells established from such primary cells by subculture over several generations. In addition, these cells may be undifferentiated embryonic stem cells, pluripotent stem cells, such as multipotent mesenchymal stem cells, unipotent stem cells, such as unipotent endothelial progenitor cells, or differentiated cells. A single type of cell may be cultured, or two or more types of cells may be cultured together.

A culture sample containing target cells is preferably subjected to dispersion treatment by which body tissue is finely ground and suspended in a liquid, separation treatment by which impurities such as cells other than the target cells and cell debris are removed from body tissue, or other forms of treatment, in advance.

Before seeding cells on a substrate, a culture sample containing target cells is preferably subjected to preliminary culture by various techniques in advance, so as to multiply the target cells. Preliminary culture can be carried out by conventional culture techniques, such as monolayer culture, culture in a coated dish, or culture on a gel. As a method of preliminary cell culture conducted by adhering cells to the surface of a support, the so-called monolayer culture technique is a means that is already known. Specifically, a culture sample and a culture solution are accommodated in a culture vessel, the culture vessel is maintained under given environmental conditions, and viable cells of given types are selectively grown while adhering to the surface of a support such as a culture vessel. The apparatus, treatment conditions, and other factors are determined in accordance with, for example, a conventional monolayer culture technique. As a material for the surface of a support to which cells adhere and grow upon, a material allowing efficient cell adhesion or growth, such as polylysine, polyethyleneimine, collagen, or gelatin, may be selected. The surface of a support, such as a glass petri dish, plastic petri dish, glass slide, glass cover, plastic sheet, or plastic film, may be coated with a chemical substance allowing efficient cell adhesion or growth (i.e., a cell adhesion factor).

After preliminary culture, the culture solution is removed from the culture vessel. Thus, unwanted components in the culture sample, such as clumped or fibrous impurities, that do not adhere to the surface of the support are removed, and viable cells adhered to the surface of the support can be selectively collected. Viable cells adhered to the surface of the support can be collected by, for example, EDTA-trypsin treatment.

The cells subjected to preliminary culture in the manner described above are seeded on a cell culture substrate in a culture solution. Methods and amounts of cells seeded are not particularly limited. For example, the method described in "*Soshiki Baiyo no Gijutsu*" ("Tissue Culture Technique") (edited by the Japanese Tissue Culture Association, issued by Asakura Publishing Co., Ltd., 1999, pp. 266 to 270) can be employed. It is preferable that cells be seeded in an amount that would not require cell growth on a cell culture substrate and that cells adhere while forming a monolayer. In general, cells are preferably seeded in such a manner that $10^4$ to $10^6$ cells are contained per ml of the culture solution or per $cm^2$ of the substrate for the following reasons. That is, cellular organization is inhibited by aggregation of cells, and this causes cellular functions to deteriorate even when cells are transferred to a target material and cultured. Specifically, about $2\times10^5$ cells are seeded per 400 $mm^2$.

It is preferable that the substrate on which cells are seeded be cultured in a culture solution and the cells be allowed to adhere to a region modified to be cell adhesive. As a culture solution, any cell culture medium that is generally used in the art can be used without particular limitation. For example, basal media described in "*Soshiki Baiyo no Gijutsu*" ("Tissue Culture Technique"), (vol. 3, edited by the Japanese Tissue Culture Association, issued by Asakura Publishing Co., Ltd., p. 581), such as MEM medium, BME medium, DME medium, αMEM medium, IMDM medium, ES medium, DM-160 medium, Fisher medium, F12 medium, WE medium, and RPMI 1640 medium, can be used in accordance with types of cells to be used. Blood serum (fetal bovine serum or the like), various growth factors, antibiotics, amino acids, and other substances may further be added to basal media. Alternatively, commercially available serum-free media, such as Gibco serum-free medium (Invitrogen), can be used, for example.

The duration of cell culture varies depending on, for example, the necessity for cell manipulation at the time of culture. It is generally 6 to 96 hours and preferably 12 to 72 hours, Culture is generally conducted at 37° C. Culture is preferably conducted in the presence of about 5% $CO_2$ with the use of a $CO_2$ cell culture incubator. After culture, the substrate is washed, cells that did not adhere thereto are washed away, and cells are allowed to adhere selectively to the cell adhesive region.

According to the present invention, conductive regions are provided in the form of a plurality of independent regions isolated by insulating regions. This enables selective application of a positive potential to a specific region and selective modification of such region into a cell-adhesive region. By seeding cells in such region, cells can be cultured while selectively adhering to such region, and regions to which specific cells are allowed to adhere and at which they are cultured can be regulated. If a positive potential is then applied to another conductive region, cells can adhere to such other region and culture can be conducted thereat. According to the present invention, therefore, two or more types of cells can be allowed to adhere to different regions on a single substrate and can be simultaneously cultured. By subjecting two or more types of cells to co-culture in different regions on a single substrate, cell-to-cell interactions can be evaluated.

(Formation of a Protein Layer)

The method of cell culture according to an embodiment of the present invention involves the use of a substrate comprising a base material having a conductive region and a non-cell-adhesive membrane coupled thereto with the aid of silane. The method comprises steps of: fixing a protein on the membrane to form a protein layer; culturing cells on the protein layer; and applying a positive potential to a conductive region, so as to separate cells together with the protein layer from the substrate.

The substrate comprising a base material having a conductive region and a non-cell-adhesive membrane coupled thereto with the aid of silane, the application of a positive potential to a conductive region, cells to be employed, and other conditions are as those employed in the method of cell culture described above.

According to this embodiment, proteins, and preferably cell-adhesive proteins, are fixed to a non-cell-adhesive membrane to form a protein layer, and cells are cultured on the protein layer. A bond between the silane layer and an organic compound constituting a non-cell-adhesive membrane is cleaved upon application of a positive potential, and at least some of the organic compound is then degraded or removed. With the utilization of such properties, cells are removed together with the protein layer from the substrate. The method according to this embodiment is the same as the method of cell culture described above, with the effect that surface properties of the substrate are modified upon application of a positive potential.

Proteins are not particularly limited, provided that such proteins can be fixed to a non-cell-adhesive membrane and cell culture can be carried out on the resulting protein layer. Examples thereof include cell-adhesive proteins, such as collagen, fibronectin, vitronectin, laminin, nidogen, tenascin, thrombospondin, von Willebrand factor, osteopontin, and fibrinogen.

According to this embodiment, cells are cultured while adhering to the protein layer to generate tissue of interest, and a positive potential is applied to the conductive region. Thus, cells can be separated together with the protein layer from the substrate, and the organized cells can be easily collected. Unlike the treatment with the use of a proteinase, such as trypsin, or chemicals, the process according to this embodiment is not complicated, and contamination is less likely to occur. In addition, cell denaturation or damage that leads to loss of the original functions of cells can be avoided.

If base material surfaces are provided with fine concave-convex configurations, various effects can be expected, depending on such concave-convex pattern configurations. Specifically, separation of cells can be carried out efficiently within a short period of time, cells can be aligned along with a concave-convex pattern, and aligned tissue can be collected. It has been known that the use of a base material provided with a fine concave-convex pattern, the speed for cell sheet formation is rapid, and the formed cell sheet can be easily separated, as described in JP Patent Publication (Kokai) No. 2008-011766 A.

Hereafter, the present invention is described with reference to the examples, although the present invention is not limited to the examples.

EXAMPLES

Example 1

1. Production of Electrode Base Material

Figure 1:
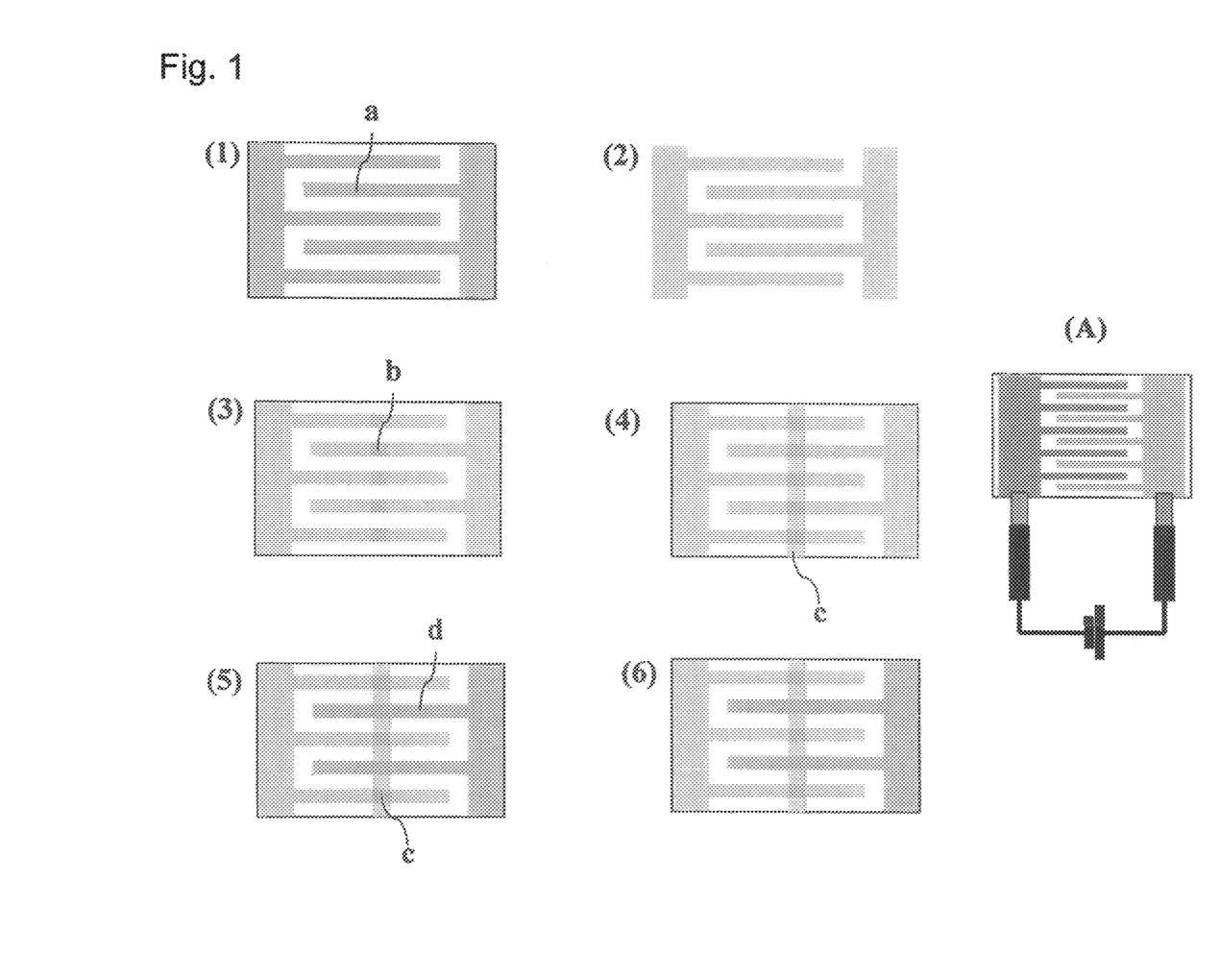
FIG. 1 illustrates the process of Example 1.

An indium tin oxide (ITO) membrane was provided on a 10 cm×10 cm square alkali-free glass to a thickness of 150 nm by sputtering, and the resulting membrane was subjected to resist coating, exposure using a photomask, development, and etching to prepare a base material provided with a comb-shaped ITO electrode with a line width of 100 μm (FIG. 1(1)). FIG. 1(1)a Shows a conductive region composed of an ITO membrane.

2. Production of Cell Culture Substrate (First-Phase Reaction)
While agitating a mixture of 39.0 g of toluene and 750 μl of epoxysilane TSL8350 (GE Toshiba Silicones Co., Ltd.), a catalytic amount of triethylamine was added thereto, and the mixture was further agitated at room temperature for several minutes. The ITO base material washed with UV application was soaked in the epoxysilane solution, followed by agitation at room temperature for 19 hours. Thereafter, the ITO base material provided with an undercoat was washed with ethanol, rinsed, and then dried.
(Second-Phase Reaction)
While agitating 15 g of tetraethylene glycol, a catalytic amount of concentrated sulfuric acid was slowly added thereto, and the mixture was further agitated at room temperature for several minutes. The base material treated with epoxysilane was soaked in the tetraethylene glycol described above, and a reaction was allowed to proceed at 80° C. for 60 minutes. After the reaction, the base material was thoroughly rinsed and then dried. Thus, a substrate upon which a hydrophilic thin membrane is provided was obtained (FIG. 1(2)).
(Oxidation)
A photomask coated, on its entire surface, with a titanium oxide-based photocatalyst was prepared. The photomask had a 250-μm-square aperture pattern at intervals of 500 m, and it was 5 inches in length provided with an aperture with a width of about 1.5 cm on its periphery. The illumination of the exposure apparatus was measured at the wavelength of 350 nm in advance, and the measured value was employed as an indication for determining the duration of exposure. The illumination was 25 mW/cm$^2$. The ITO substrate upon which a hydrophilic thin membrane is provided and the quarts plate provided with a catalyst were positioned in such a manner that a hydrophilic thin membrane was opposed to a photocatalyst layer of the photomask and that the comb-tooth region in the comb-shaped conductive region of the ITO substrate was orthogonal to the squared pattern of the photomask. The photomask was positioned inside the exposure apparatus, so that the substrate would be irradiated with light from the back of the photomask. The resultant was exposed to light for 120 seconds for oxidation, and the hydrophilic thin membrane was subjected to partial degradation (FIG. 1(3)b). Thereafter, the membrane was cut into 25 mm×25 mm square pieces for convenience of culture,

3. Cell Culture

The substrate cut in the manner described above was sterilized with ethylene oxide gas. Sterilized cloning rings (ϕ8 mm) were embedded in the substrate, and mouse fibroblasts (5×10$^4$ cells) were seeded therein. Culture was conducted using DMEM medium containing 10% serum in an incubator at 37° C. in the presence of 5% $CO_2$ for 24 hours. As a result of observation under a phase-contrast microscope, cells were found to adhere selectively to the oxidated regions in the confluent state (FIG. 1(4)c).

4. Application of Electric Potential

Figure 2:
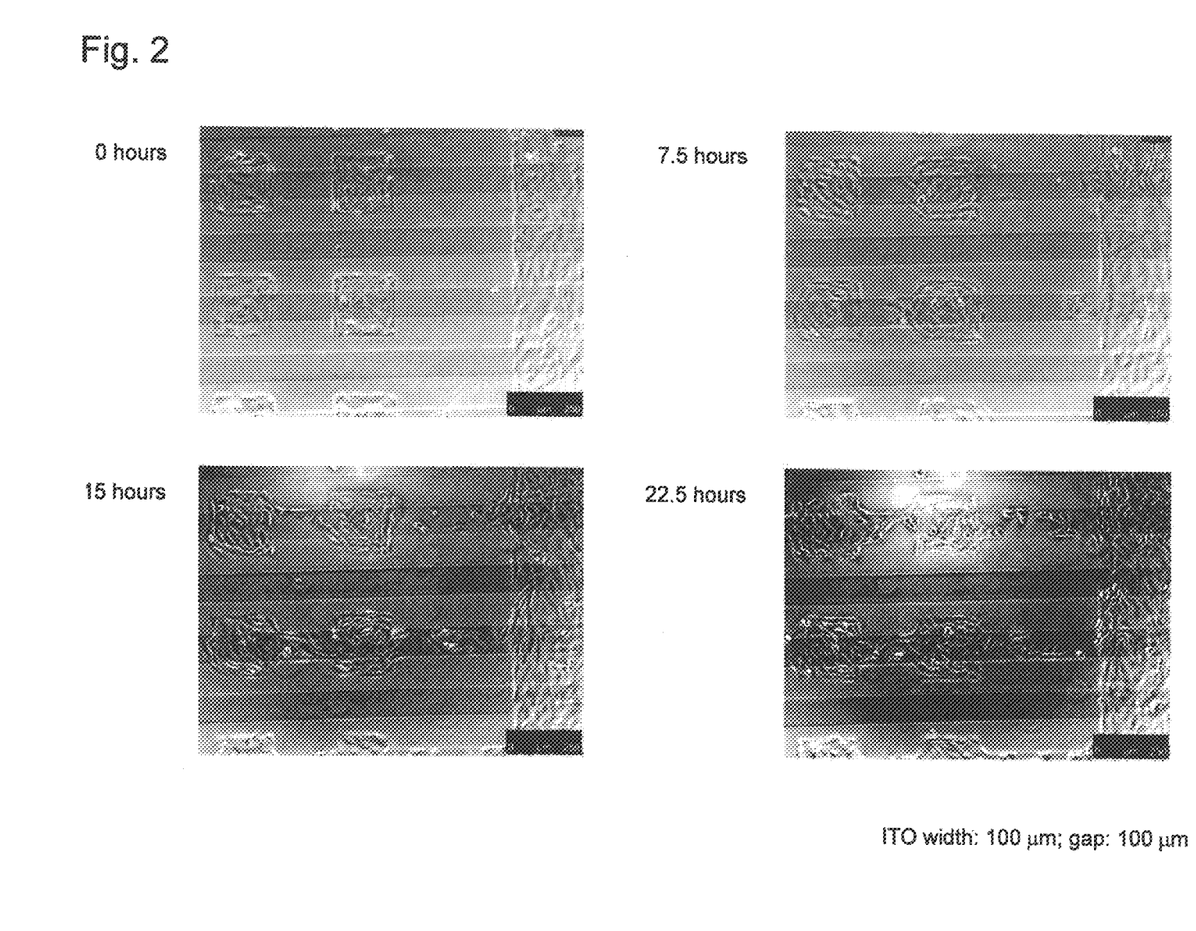
FIG. 2 shows a photograph showing the test results of electric potential application (2 V, 1 minute), indicating that, upon application of a positive potential to a conductive region of a substrate, a non-cell-adhesive membrane is separated therefrom, the region is converted into a cell-adhesive region, and cells migrate and newly adhere thereto.

The comb-shaped ITO substrate was connected to a circuit and an electric potential of +2V was applied for 2 minutes (FIG. 1 (A)). With the elapse of time, the hydrophilic thin membrane was separated selectively from the electrode to which a positive potential had been applied (FIG. 1(5)d), and the cells that had adhered in accordance with the square pattern of the photomask were observed to migrate while deforming the pattern (FIG. 1(6) and FIG. 2). Such cells were observed to have migrated about 100 μm on a 100-μm-wide electrode and adhered thereto 7.5 hours later.

Example 2

Example 2 comprises steps of; introducing an epoxy group on a glass surface; allowing polyethylene glycol (PEG) to form a covalent bond with the epoxy group; allowing succinic anhydride to react with a hydroxyl group existing at a free end of the PEG to form a carboxyl group; converting the carboxyl group into active ester; allowing a protein to react with active ester; and inactivating unreacted active ester with the aid of ethanolamine. A specific procedure is as described below,

1. Production of Electrode Base Material

Figure 3:
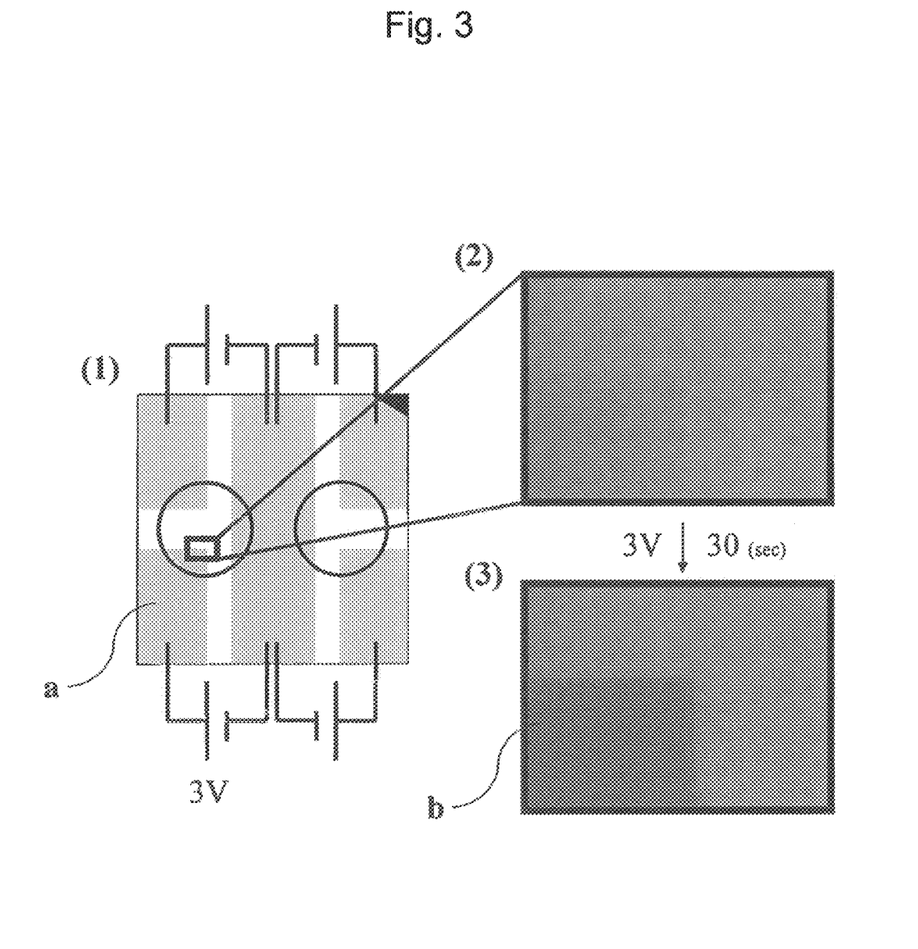
FIG. 3 shows that, upon application of a positive potential to a substrate on which a protein layer is formed, the protein layer is separated from the substrate.

An indium tin oxide (ITO) membrane was provided on a 10 cm×10 cm square alkali-free glass to a thickness of 150 nm by sputtering, and the resulting membrane was subjected to resist coating, exposure using a photomask, development, and etching to prepare a base material comprising a conductive region composed of an ITO membrane with a pattern as shown in FIG. 3(1) (FIG. 3(1)), FIG. 3(1)a shows a conductive region composed of an ITO membrane.

2. Formation of Hydrophilic Thin Membrane

While agitating a mixture of 39.0 g of toluene and 750 epoxysilane TSL8350 (GE Toshiba Silicones Co., Ltd.), a catalytic amount of triethylamine was added thereto, and the mixture was further agitated at room temperature for several minutes. The ITO base material washed with UV application was soaked in the epoxysilane solution, followed by agitation at room temperature for 19 hours. Thereafter, the ITO base material provided with an undercoat was washed with ethanol, rinsed, and then dried.
While agitating 15 g of PEG 4000 (Kanto Chemical Co., Inc.), a catalytic amount of concentrated sulfuric acid was slowly added thereto, and the mixture was further agitated at room temperature for several minutes. The base material treated with epoxysilane was soaked in the PEG solution, and the reaction was allowed to proceed at 80° C. for 60 minutes. After the completion of the reaction, the base material was thoroughly rinsed and then dried. Thus, a covalent bond was formed between PEG and the epoxy group,

3. Provision of Amine-Reactive Group

Subsequently, 50 mg of succinic anhydride (SuA, Kanto Chemical Co., Inc.) and 60 mg of 4-dimethylaminopyridine (DMAP, Wako Pure Chemical Industries, Ltd.) were dissolved in 43 g of toluene, and the substrate was soaked therein and heated at 80° C. for 1 hour. Subsequently, the substrate was washed with ethanol and with water, followed by blow-drying with nitrogen. The ring-opening half-esterification reaction advanced in this step and carboxyl groups were introduced on the free ends of the PEG. Subsequently, 58 mg of N-hydroxysuccinimide (NHS, Wako Pure Chemical Industries) and 78 μl of N,N'-diisopropylcarbodiimide (DIC, Wake Pure Chemical Industries) were dissolved in 43 g of toluene, and the substrate was soaked therein and heated at 80° C. for 1 hour. Thereafter, the substrate was washed with ethanol and with water, followed by blow-drying with nitrogen. Thus, N-hydroxysuccinimide (NHS) groups were introduced on the free ends of PEG.

4. Formation of a Protein Layer

At the outset, the substrate was brought into contact with a FITC-BSA solution (5 mg/ml, a 1:1 mixture of PBS and glycerol) and incubated at room temperature for 10 minutes. Thus, active esters on the substrate surface were allowed to react with HRPs, and FITC-BSA was fixed on the substrate surface. Subsequently, the substrate surface was washed three times with 0.05% Tween 20-containing PBS (hereafter, referred to as "wash buffer"), brought into contact with 50 mM ethanolamine (EA), and then incubated at room temperature for 10 minutes. Thus, unreacted active esters were substantially completely inactivated. After the substrate was washed three times with the wash buffer, FITC fluorescence was observed under a fluorescent microscope (FIG. 3(2)).

5. Application of Potential

The ITO conductive region was connected to the circuit, and potentials of +3V were applied for 30 seconds. With the elapse of time, fluorescence quenching of FITC was observed selectively on electrodes to which positive potentials had been applied, which indicates the separation of the protein layer (FIG. 3 (3)b).

Comparative Example

Figure 4:
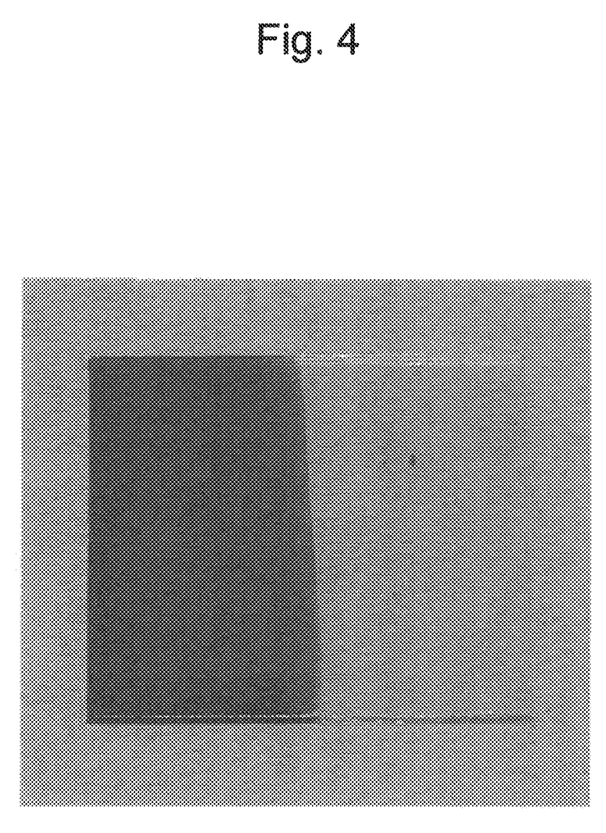
FIG. 4 shows a photograph showing that, upon application of a negative potential to an indium tin oxide (ITO) membrane on the base material surface, a transparent ITO membrane becomes black.

An indium tin oxide (ITO) membrane was provided on a 10 cm×10 cm square alkali-free glass to a thickness of 150 nm by sputtering. A negative potential of −3V was applied selectively to a left half of the membrane for 2 minutes. As a result, blackening of the ITO membrane, which was initially transparent, was observed (FIG. 4).

All publications, patents, and patent applications cited herein are incorporated herein by reference in their entirety.

The invention claimed is:

1. A method of cell culture comprising: applying a positive potential to a conductive region of a substrate comprising a base material having a conductive region and a non-cell-adhesive membrane coupled thereto with the aid of silane, so as to separate the non-cell-adhesive membrane from the substrate; and culturing cells in a region from which the non-cell-adhesive membrane has been separated.

2. The method according to claim 1, wherein the conductive region comprises an indium tin oxide membrane on the base material surface.

3. The method according to claim 1 wherein the non-cell-adhesive membrane is a non-cell-adhesive hydrophilic membrane composed of an organic compound.

4. The method according to claim 3, wherein the organic compound is an alkylene glycol oligomer.

5. The method according to claim 1, wherein a positive potential of 1 to 10 V is applied to the conductive region.

6. The method according to claim 1, wherein the positive potential is applied for 0.5 to 60 minutes.

7. A method of cell culture comprising: fixing a protein on a membrane of a substrate comprising a base material having a conductive region and a non-cell-adhesive membrane coupled thereto with the aid of silane, so as to form a protein layer; culturing cells on the protein layer; and applying a positive potential to the conductive region, so as to separate cells together with the protein layer from the substrate.

8. The method according to claim 7, wherein the conductive region comprises an indium tin oxide membrane on the base material surface.

9. The method according to claim 7, wherein the non-cell-adhesive membrane is a non-cell-adhesive hydrophilic membrane composed of an organic compound.

10. The method according to claim 9, wherein the organic compound is an alkylene glycol oligomer.

11. The method according to claim 7, wherein a positive potential of 1 to 10 V is applied to the conductive region.

12. The method according to claim 7, wherein the positive potential is applied for 0.5 to 60 minutes.

* * * * *